US011103407B2

(12) United States Patent
Zahynacz

(10) Patent No.: US 11,103,407 B2
(45) Date of Patent: Aug. 31, 2021

(54) UNIVERSAL RAIL CLAMP

(71) Applicant: Smith & Nephew, Inc., Memphis, TN (US)

(72) Inventor: Daniel Zahynacz, Somerville, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 17/106,495

(22) Filed: Nov. 30, 2020

(65) Prior Publication Data

US 2021/0077330 A1    Mar. 18, 2021

Related U.S. Application Data

(63) Continuation of application No. 16/632,758, filed as application No. PCT/US2018/043674 on Jul. 25, 2018, now Pat. No. 10,874,571.

(60) Provisional application No. 62/536,636, filed on Jul. 25, 2017.

(51) Int. Cl.
| *A61G 13/10* | (2006.01) |
| *F16B 2/12* | (2006.01) |
| *F16B 2/18* | (2006.01) |
| *A61B 90/57* | (2016.01) |

(52) U.S. Cl.
CPC ............ *A61G 13/101* (2013.01); *F16B 2/12* (2013.01); *F16B 2/185* (2013.01); *A61B 2090/571* (2016.02)

(58) Field of Classification Search
CPC combination set(s) only.
See application file for complete search history.

(56) References Cited

U.S. PATENT DOCUMENTS

| 5,741,210 | A  | * | 4/1998 | Dobrovolny | ........... A61B 17/02 600/227 |
| 6,622,980 | B2 | * | 9/2003 | Boucher | ................. F16B 2/185 248/231.51 |
| 7,003,827 | B2 | * | 2/2006 | DeMayo | ................. A61G 13/10 248/229.14 |
| 7,156,806 | B2 | * | 1/2007 | Dobrovolny | ........... A61B 17/02 403/322.1 |
| 7,159,832 | B2 | * | 1/2007 | Easterling | ............... A61G 15/10 24/455 |
| 8,011,629 | B2 | * | 9/2011 | Herskovic | .............. F16M 13/02 248/230.1 |
| 8,485,509 | B2 | * | 7/2013 | Wang | ...................... B24B 41/06 269/249 |
| 8,740,163 | B1 | * | 6/2014 | Taylor | ................... F24S 25/636 248/237 |

(Continued)

*Primary Examiner* — Monica E Millner
(74) *Attorney, Agent, or Firm* — Norman F. Hainer, Jr.

(57) ABSTRACT

A clamping assembly for adjustably connecting a device to a rail, including a clamp body, rail interface mechanism, and support mechanism for the device. The rail interface mechanism attaches to rails of various heights and thicknesses with a single user control activation. The rail interface mechanism includes at least one flanged fixed upper jaw, a rail clamp control comprised of a threaded vertical axle terminating in a pin end, a flanged lower jaw constrained to slidable vertical motion along an internal face of the clamp body by the pin end of the vertical axle, and two angled wedges that can be extended and retracted horizontally.

20 Claims, 8 Drawing Sheets

(56) References Cited

U.S. PATENT DOCUMENTS

| | | | |
|---|---|---|---|
| 9,022,334 B1* | 5/2015 | DeMayo | F16M 13/022 |
| | | | 248/229.22 |
| 9,615,987 B2* | 4/2017 | Worm | A61G 13/1245 |
| 9,873,244 B1* | 1/2018 | Jurman | B41F 15/36 |
| 9,993,381 B2* | 6/2018 | Blackwell | A61G 13/125 |
| 10,357,416 B2* | 7/2019 | Cole | A61G 13/124 |
| 10,478,363 B2* | 11/2019 | Koch | A61G 13/101 |
| 10,478,364 B2* | 11/2019 | Fossez | A61G 13/1245 |
| 10,617,586 B2* | 4/2020 | Katzenstein | A61G 13/101 |
| 10,716,726 B2* | 7/2020 | Bergman | A61G 7/05 |
| 10,987,193 B2* | 4/2021 | Chen | A61G 13/101 |
| 2012/0126079 A1* | 5/2012 | Russell | A61G 13/101 |
| | | | 248/229.23 |
| 2012/0241571 A1* | 9/2012 | Masionis | A61G 1/04 |
| | | | 248/214 |
| 2016/0296401 A1* | 10/2016 | Cole | A61G 13/101 |
| 2016/0361219 A1* | 12/2016 | Herrig | F16B 2/12 |
| 2019/0100150 A1* | 4/2019 | McFadden | B60R 9/058 |

* cited by examiner

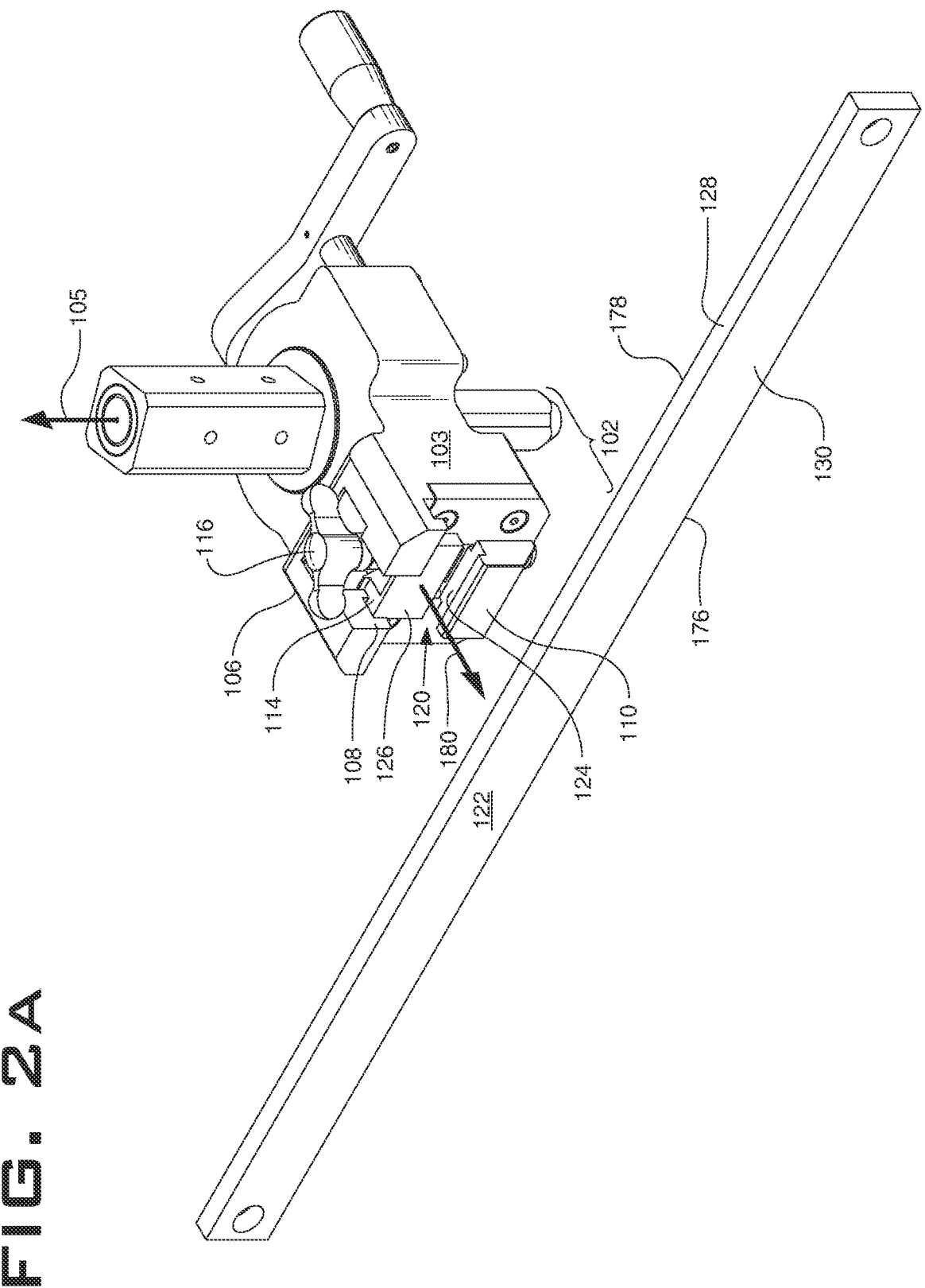

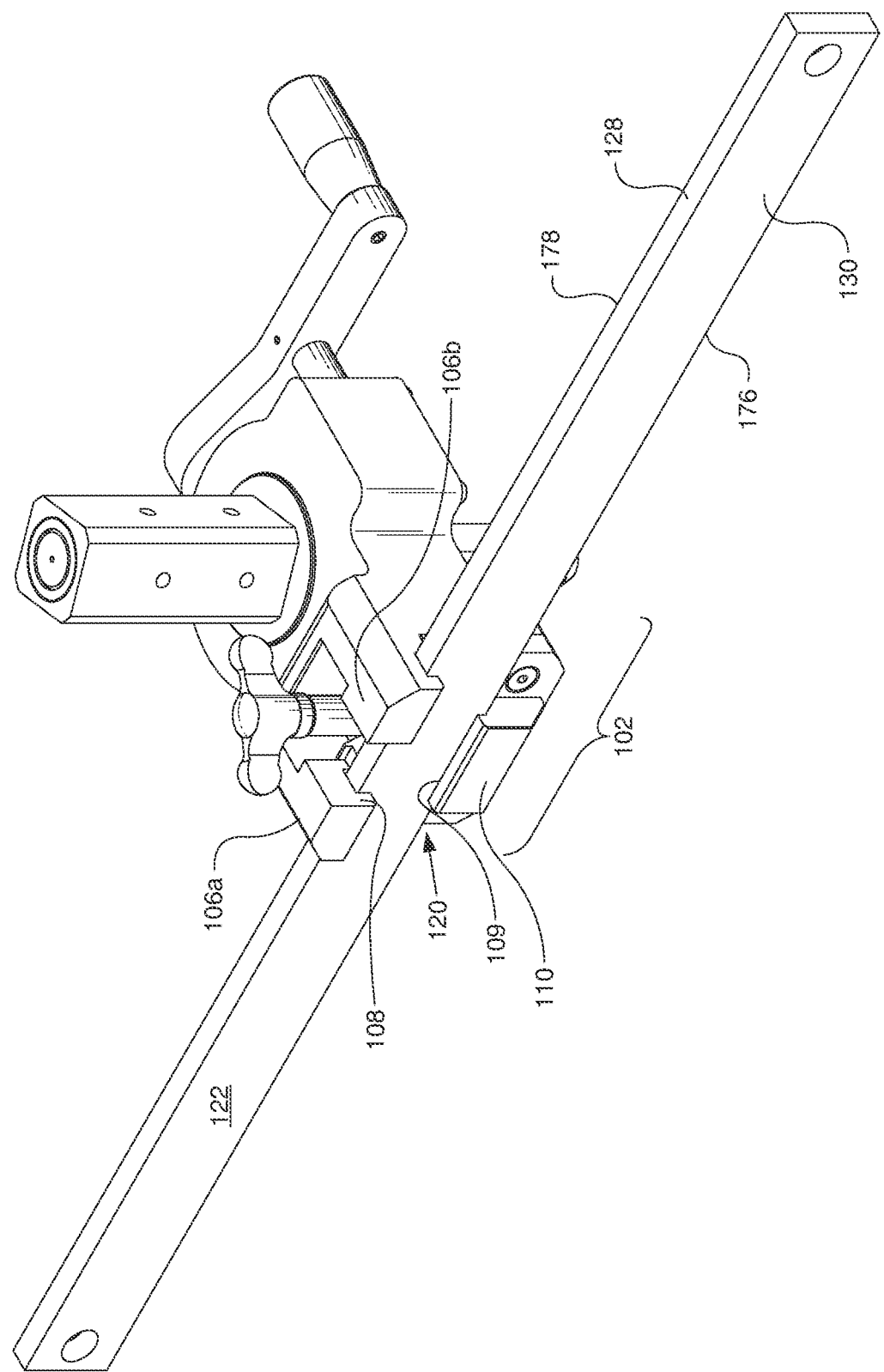

UNIVERSAL RAIL CLAMP

CROSS-REFERENCE TO RELATED APPLICATIONS

This application is a continuation of Ser. No. 16/632,758 filed Jan. 21, 2020, which is a 371 application of PCT/US18/043674 filed Jul. 25, 2018, which claims priority to and benefit of U.S. Provisional Application No. 62/536,636, filed Jul. 25, 2017, the contents of which are incorporated herein by reference in their entirety for all purposes.

BACKGROUND

Technical Field

The present invention relates to medical device or accessory mounting systems including a quick release clamp for use on operating room (OR) tables or hospital bed rails of varying heights and thicknesses, while providing rotational control of the device about a set axis.

Background

In many instances, it is desirable (if not required) to attach a medical device or accessory to a bedrail of the surgical/medical bed. Rails, such as those found on Operating Room (OR) tables and hospital beds, are a convenient location for such mounting. Securing devices or accessories is critical for translating the stability provided by the table to the device or accessory and ultimately to, for example, a surgical site, which is essential for precision access and control of surgical tools and instruments by the surgeon. Typical clamps are designed to fit specific rail geometry in terms of height and thickness, requiring medical facilities to carry a variety of clamps. Typical clamps are also limited to tightening in only one degree of freedom.

In addition to stability, table or bed rail clamps can provide rotational control to a vertical support. This is often achieved by threading a pin, screw or toothed fixture against the vertical support, which connects a medical device to the rail clamp. Typical rail clamp rotational controls require two separate activations, one for locking and releasing rotational control and a second for performing the actual rotation of the device.

Many types of clamping devices have been devised for attachment on to bed rails for securely holding the hospital accessories and/or medical instruments. Many have been configured to engage the end of the bed rail and then be slid into the desired position. A common problem with such bed rail clamps arises when multiple accessories must be attached to the bed rail in a surgical/medical procedure. For example, when two bed rail clamps are already positioned on a bed rail, and a third bed rail clamp must be positioned between the first two, moving the third bed rail clamp into position can be quite challenging. Other conventional clamp devices are "C" shaped, with jaws that pivot about the rail, or more complex screw rail clamps with articulating arms for more precise placement and positioning. The clamps are typically capable of receiving various sized instruments and securely attaching the instruments onto hospital bed rails of varying sizes and heights. However, many known rail clamps are not designed to be clamped quickly or are too cumbersome for fast clamping. Clamps typically require several motions and adjustments before being able to secure an instrument to a rail, as hospital rails vary in height and shape from one bed to another.

Thus, there is a need in the art for improved OR table or bed rail clamping devices and systems that allow rapid installation while accommodating variations in the rail characteristics.

SUMMARY

Embodiments disclosed herein provide universal clamp assemblies permitting a medical device or accessory to be attached to a range of OR table or hospital bed side rails of widely varying heights and thicknesses. The clamp assembly embodiments provide a single user operable actuator for securing horizontally and vertically a rail interface to the bedrail, and an integrated rotational connector user operable by a single distinct actuator for rotational control of a vertical support to which the device or accessory may be mounted. The embodiments provide the ability to attach the clamp and device at any location along the length of the OR table side rail, unlike conventional clamps that often require attachment at the end of the OR table side rail or at defined breaks along the OR table side rail, which then requires additional steps to bring the device into the desired location for setup. The clamp assembly also advantageously allows positioning of the supported device or accessory with an upright orientation, permitting the balanced transfer of weight from the user to the bed rail.

In one embodiment, a clamping assembly includes a clamp body, a rail interface mechanism dimensioned to receive a table or bed rail ("bedrail" will be used herein to cover both, and other, types of rails) and rotating connector mechanism coupled to the clamp body and including a vertical support to which the device or accessory may be connected. The rail interface mechanism may be comprised of at least one fixed jaw preferably including a flange, a rail clamp control including a control knob or other user operable actuator, and a threaded vertical axle rotatably coupled to the clamp body and having a pin end and another end connected to the rail clamp control. The rail interface mechanism further includes a flanged sliding lower jaw opposing the fixed jaw and constrained to slidable vertical motion along an internal face of the clamp body. The sliding lower jaw is supported and vertically constrained by the pin end of the threaded vertical axle. A threaded wedge is restricted to sliding motion in the vertical direction and is threadably coupled (e.g., by a threaded cavity or bore) to threads of the vertical axle, and includes an angled wedge face sloping downward toward the internal face of the clamp body. The rail interface further includes a floating wedge constrained to motion in a horizontal direction, and having a wedge face parallel and operatively coupled to the angled wedge face of the threaded wedge.

During clamping operation, rotating the rail clamp control causes the sliding jaw to slide vertically to secure the rail between the fixed jaw and the sliding jaw. Further actuating the rail clamp control causes the threaded wedge to slide vertically, such that a force imparted from the wedge face of the threaded wedge to the wedge face of the floating wedge urges the floating wedge to move horizontally to secure the rail horizontally between the floating wedge and the flanges of the fixed jaw and the sliding jaw. Thus, with a single adjustment, both vertical and horizontal clamping of the bedrail is effectuated.

The threaded wedge and floating wedge may be restricted, respectively, to vertical and horizontal sliding by abutting respective internal surfaces of the clamp body, which may include non-integrated wedge sliding track components. The sliding lower jaw may have a curved (e.g., U-shaped) cut for rotatably receiving an end of the vertical axle, such that the pin end has a dimension larger than the curved cut so as to constrain downward vertical motion of the lower jaw.

The rotational connector provides a mechanism for vertical support for the medical device and/or accessory, and includes in one embodiment a vertical support member extending from the clamp body and constrained to rotational motion about a vertical axis by a cylindrical shaft secured on a first end to the support member, where the cylindrical shaft extends at least partially through the clamp body. The cylindrical shaft is secured to a shaft gear that, in turn, is operably coupled to a horizontally disposed worm screw including an axle constrained to rotational motion and extending on one end to an area external to the clamp body. A user control may be fixed to the end of the worm screw axle, such that rotation of the worm screw axle via the user control, permits rotational adjustments to the vertical support member.

In a further example embodiment a clamping assembly is disclosed for adjustably connecting a device to a rail, the assembly having a clamp body and a rail interface mechanism. The rail interface mechanism is dimensioned to receive a rail, such as a bed rail, and includes a first and second jaw defining a mouth, the second jaw vertically slideable relative to the first jaw so as to alter the size of the mouth opening. The rail interface mechanism also has a rail clamp control with a threaded vertical axle, and a pin end, the vertical axle rotatably coupled to the clamp body. The vertical axle extends through the second jaw. The rail interface mechanism also includes a threaded wedge and a floating wedge, the threaded wedge restricted to a vertical sliding motion and the floating wedge restricted to horizontal sliding motion. The threaded wedge is threadably coupled to threads of the vertical axle. The threaded wedge includes an angled wedge face sloping downward toward an internal face of the clamp body that is operatively coupled to a wedge face of the floating wedge so as to drive the horizontal motion of the floating wedge. The wedge face of the floating wedge is orientated parallel with the angled wedge face of the threaded wedge. Rotating the rail clamp control causes the rail interface to move the second jaw and further causes the floating wedge to move horizontally to secure the rail horizontally between the floating wedge and the first and second jaws. The clamp assembly includes a vertical support mechanism coupled to the clamp body and distinct from the rail interface mechanism, the vertical support mechanism providing rotational control of a device. The first jaw may be a fixed jaw. The first and second jaw may further comprise flanges configured to interface with an outer surface of the rail and further retain the rail. The first jaw may be split into two portions separated by an opening there-between. The vertical axle may extend through an opening in the second jaw, the pin end sized larger than the second jaw opening so as to engage the second jaw and cause translation of the second jaw. Rotating the rail clamp control may cause the threaded wedge to slide vertically, such that a force imparted from the wedge face of the threaded wedge to the wedge face of the floating wedge urges the floating wedge to move horizontally.

The vertical support mechanism may include a vertical support member extending from the clamp body and constrained to rotational motion about a vertical axis by a cylindrical shaft secured on a first end to the support member, the cylindrical shaft extending at least partially through the clamp body. The vertical support mechanism may include a shaft gear secured to a second end of the cylindrical shaft, a horizontally disposed worm screw, operably engaging the shaft gear. The worm includes an axle constrained to rotational motion and extending on one end of the worm screw to an area external to the clamp body. A user control is fixated to the end of the worm screw axle, such that rotation of the worm screw axle via the user control permits rotational adjustments to the vertical support member. The worm screw may operably engage the second end of the shaft at a lower lead angle of the worm screw. The worm screw and gear are configured to reduce back-drive.

The disclosure may further describe a method of attaching a rail interface mechanism of a clamping assembly to a rail, including the steps of hooking an upper jaw of the interface mechanism over a top surface of the rail, the upper jaw have a flange configured to aid in the step of hooking, and rotating a vertical axle of the interface mechanism so as to draw a lower jaw vertically towards the upper jaw and engage a bottom surface of the rail and wherein rotating the vertical axle also moves a surface of the rail interface mechanism horizontally so as to engage a side surface of the rail. The method may further include rotating a horizontal axle of the clamping assembly so as to rotationally control a vertical shaft. The vertical shaft may be selectively coupled to a medical device. The horizontal axle may be coupled to a worm of a worm drive. The worm of the worm drive may have a low lead angle, configured so as to reduce back drive from the vertical shaft. The vertical shaft may be coupled to a worm screw of a worm drive.

BRIEF DESCRIPTION OF THE DRAWING

The foregoing and other objects, features and advantages will be apparent from the following, more particular description of the embodiments, as illustrated in the accompanying figures, wherein like reference characters generally refer to identical or structurally and/or functionally similar parts throughout the different views. The figures are not necessarily to scale, emphasis instead being placed upon illustrating the principles of the embodiments, wherein:

FIGS. 2A-2C are illustrations of stages of clamping an embodiment of the universal clamping assembly to a bedrail;

DETAILED DESCRIPTION

The following descriptions of embodiments of rail clamping assemblies are merely exemplary in nature, and are in no way intended to limit the disclosed embodiments or their applications or uses. Alternatives to the embodiments disclosed may be devised without departing from the scope of the disclosure.

Well-known elements of technologies associated with the embodiments will not be described in detail, or will be omitted, so as not to obscure the relevant details of the novel methods and apparatus. The word "exemplary" is used herein to mean "serving as an example, instance, or illustration." Any embodiment described herein as "exemplary" is not necessarily to be construed as preferred or advantageous over other embodiments. Likewise, the term "embodiment" and the descriptive language associated with each use of the term do not require that all embodiments include the discussed feature, limitation, advantage or mode of operation. As used herein, the singular forms "a", "an" and "the" are intended to include the plural forms as well, unless the context clearly indicates otherwise. It will be further understood that the terms "comprises", "comprising", "having", "includes" and/or "including", when used herein, specify the presence of stated features, steps, operations, elements, and/or components, but do not preclude the presence or addition of one or more other features, steps, operations, elements, components, and/or groups thereof. Further, the phrase "based on" is intended to mean "based, at least in part, on" unless explicitly stated otherwise. The terms "upper" and "lower" are meant to convey relative positioning, and not absolute positioning with respect to ground, in that the rail to which the clamping assembly is clamped is typically, but not necessarily horizontally disposed with respect to a bed or table.

Figure 1:
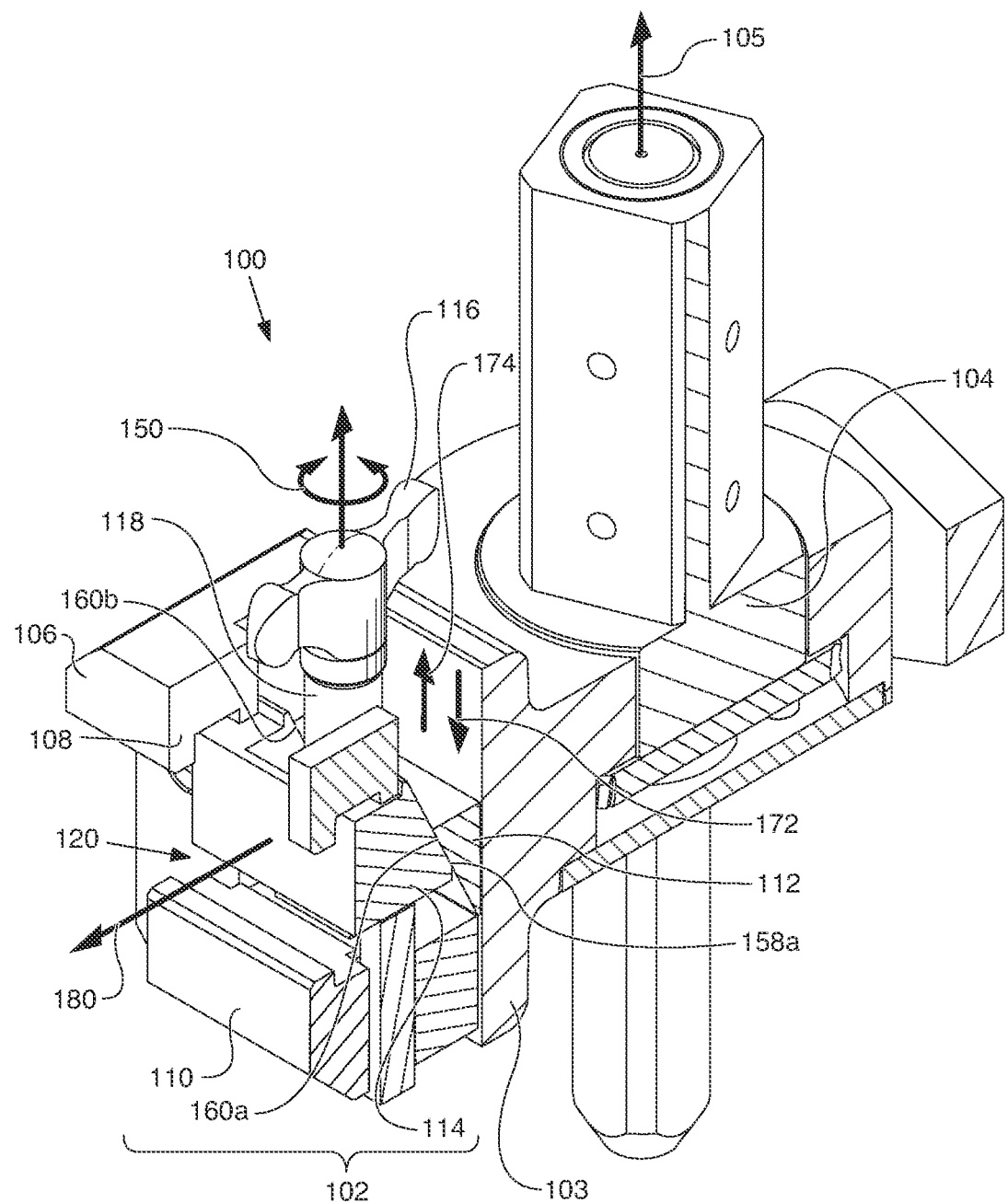
FIG. 1 is an illustration of a cutaway view of an exemplary embodiment of a universal clamp assembly.

FIG. 1 is a cutaway view (with one side of an upper jaw component removed to expose internal components) of a quick release clamping assembly 100 that has been adapted for use on a rail of, for example, an operating table or bed. The clamping assembly 100 may be configured with two coupled mechanisms, a side rail interface mechanism 102 and a rotational connector mechanism 104 that provides rotational control of a medical device (not shown) mounted thereto. The side rail interface mechanism 102 allows for quick installation and release on a rail by activating a single user control for simultaneous tightening and loosening of vertical and horizontal jaws. The rotational connector mechanism includes a single rotational user control that provides rotational control for a supported medical device of accessory about a fixed axis 105. According to the embodiment, there is no need for clearance space to position and tighten screws or other such features, either above or below the bed rail.

The embodiment of rail interface mechanism 102 includes a clamp body 103 and a set of jaws dimensioned to adjustably receive a range of rectangle-shaped rails. Example rail dimensions may vary from approximately 0.2 inches×1.5 inches to 0.4 inches×1.0 inches, with ratios of height:width up to 8:1, and as little as 2:1. The jaws may include at least one fixed (upper) jaw 106 which may include a flange 108 to improve securement of the rail. As shown the upper jaw 106 has an opening (seen best in FIG. 3B), splitting the upper jaw 106 into two portions (106a and 106b), disposed approximately equidistant from axle 118. The jaws may also include a vertically sliding lower jaw 110 that is aligned substantially with the opening between to two portions 106a and 106b of the upper jaws. Lower jaw 110 as shown is slightly larger than opening between the upper jaw portions so as to constrain lower jaw horizontally. Lower jaw 110 may also include a flange 109, both flanges 108, 109 defining legs that extend towards each other along the same plane and wherein both flanges 108, 109 are configured to engage a portion of an outer surface of a rail (shown in FIG. 2A as 130). The jaws may also include two angled wedges, a threaded wedge 112 and a floating wedge 114 that can be retracted and extended horizontally. In this embodiment, a single actuating member, user control knob 116, is attached to a threaded vertical axle 118.

Figure 2B:
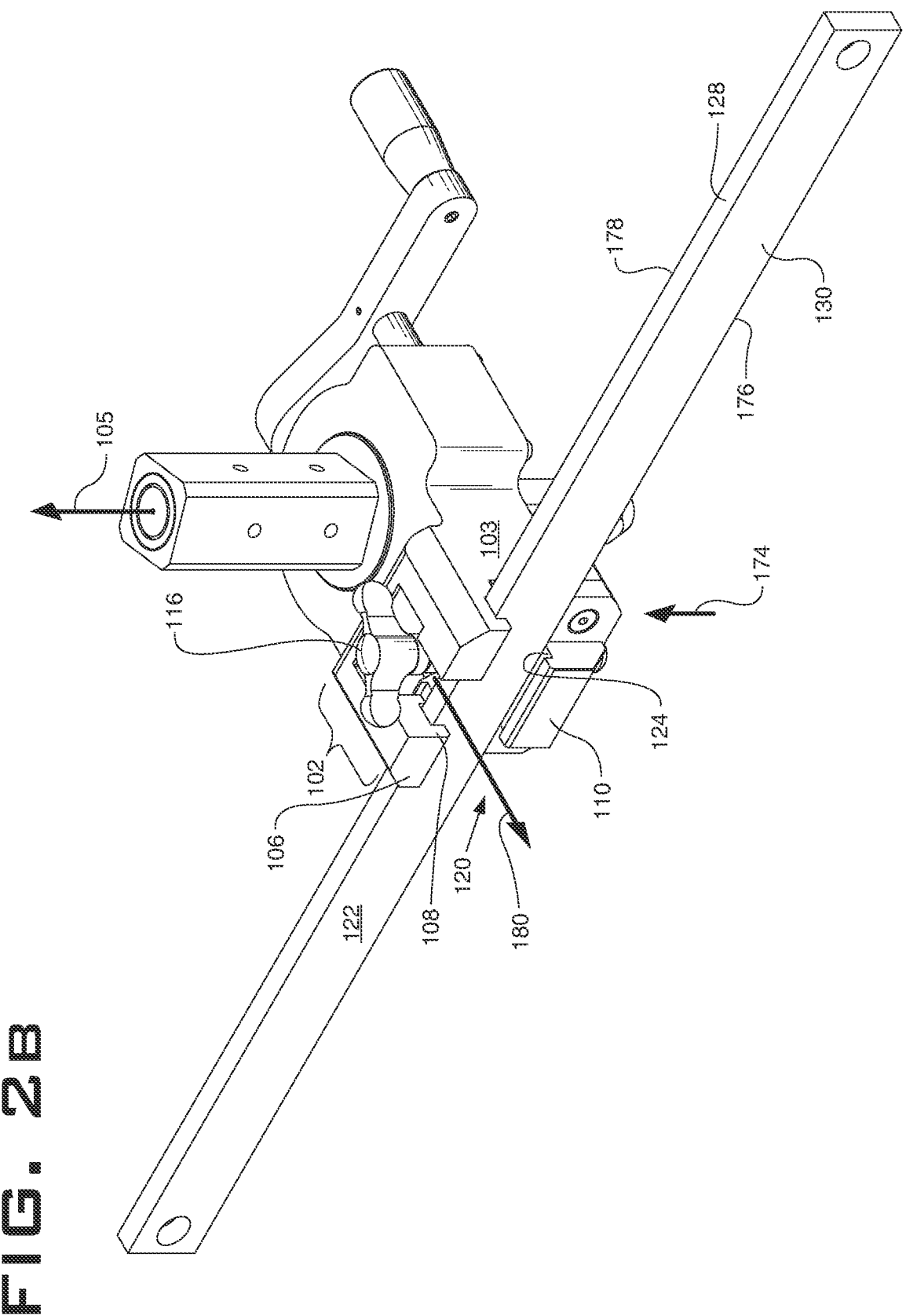

A mouth 120 is defined proximate the clamp body 103 by the jaws and wedges, wherein the mouth 120 is capable of receiving a bed rail 122 (such as shown in FIG. 2A-2C) or other features of the bed or table (not shown) to which the rail interface 102 can be attached. It should be appreciated that while the mouth 120 is illustrated as having a rectangle shaped cross-section, in alternative embodiments with suitably contoured flange(s) 108 of fixed jaw(s) 106, surface 124 of lower jaw 110, and surface 126 of floating wedge 114, mouth 120 could be configured to have a cross-section of any suitable shape. The components of the rail interface mechanism 102 may be made of any suitable rigid material, such as metal, for example, which may immovably affix to the rail 122 when compressed against the rail 122.

It should be appreciated that lower jaw 110 and fixed upper jaw(s) 106 may be made of the same or different materials. Moreover, an abrasive and/or adhesive material, or any other suitable material, may be used to prevent the jaws 106, 110 and floating wedge 114 from slipping or sliding off along the rail 122, or alternatively to aid in easy sliding, without gullying. Further, the jaws 106, 110 and floating wedge 114 may be made of any material (e.g., rubber, polyurethane, or other non-slip material or coating, etc.) that may provide a suitable degree of compressibility when rail interface mechanism 102 is secured onto rail 122.

FIGS. 2A-2C illustrate the rail interface mechanism 102 in the process of clamping onto the bedrail 122. The rail interface mechanism 102 is oriented such that the mouth 120 engages four sides of the bedrail 122, such that the bedrail 122 is located in the mouth 120. The rail interface mechanism 102 may first engage the bedrail 122 such that the rail interface mechanism 102 is supported by the bedrail 122 without falling off, even though the rail interface 102 has not yet been secured thereto, such as shown in FIG. 2B, showing lower jaw 110 spaced away or in relaxed contact with the rail 122. In the depicted exemplary orientation, the fixed upper jaw(s) 106 rest on the top surface 128 of the bedrail 122. The upper jaw(s) 106 extends over the top surface 128 of the bedrail 122 and flange 108 extends downward to engage rail surface 130, thus keeping the rail interface mechanism 102 and thereby the clamping assembly 100 from sliding or falling off the bedrail 122. Thus, the upper jaw(s) 106 allows the rail interface mechanism 102 to be easily hooked onto the bedrail 122 and held in place to facilitate the one-handed operation of control knob 116. At the above-described stage of attaching the clamping assembly 100 to the bedrail 122 shown in FIG. 2B, the control knob 116 has not yet been rotated and the sliding lower jaw 110 is not fixedly engaged to the bedrail 122.

Figure 3A:
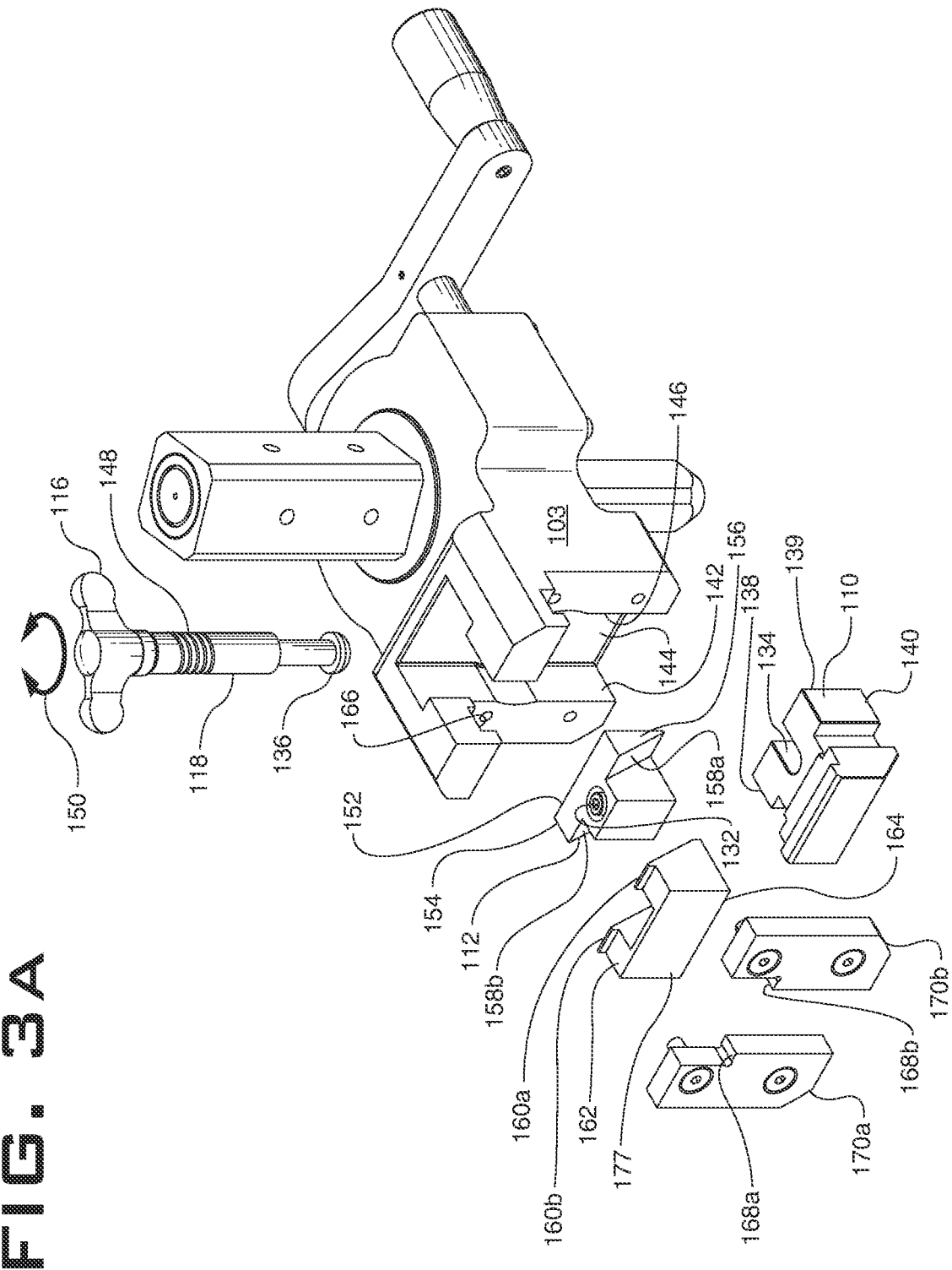
FIG. 3A is an illustration of an exploded view of an embodiment of a rail interface.
Figure 3B:
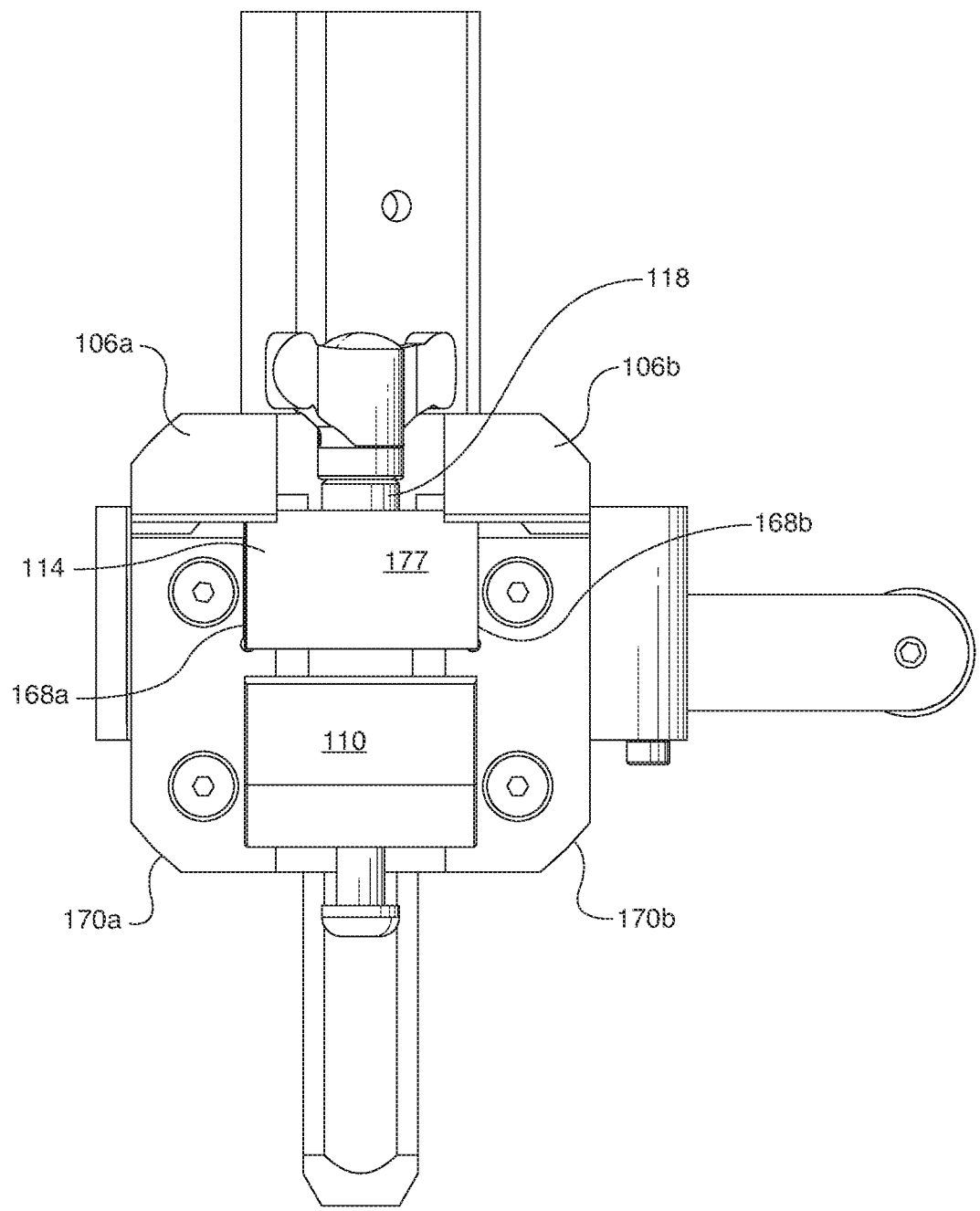
FIG. 3B is an illustration of an end view of an embodiment of a rail interface.

With reference to the exploded view of FIG. 3A, in the assembled state, the vertical axle 118 passes through a threaded bore 132 in the threaded wedge 112 and a U-shaped cut 134 in lower jaw 110. The vertical axle 118 terminates below lower jaw 110 with a pin end 136 that restricts lower jaw 110 in the vertical direction. The lower jaw 110 is fully restricted horizontally by the abutting of its vertically oriented surfaces 138,139,140 against corresponding inner surfaces 142,144,146 of clamp body 103, but is free to slide vertically along the clamp body inner surfaces 142,144,146. Stated otherwise lower law 110 is sized so as to fit within and abut a cavity defined by vertically oriented surfaces 142, 144 and 146, such that vertically oriented surface 138 abuts surface 142, vertically oriented surface 139 abuts surface 144 and vertically oriented surface 140 abuts surface 146. The U-shaped cut 134 in the sliding lower jaw 110 allows vertical axle 118 to rotate, which in turn retracts and extends the sliding lower jaw 110 vertically as a result of the interaction of the threaded bore 132 of the threaded wedge 112 and mateable threads 148 on the vertical axle 118.

In the assembled state, the threaded wedge 112 is fully restricted horizontally by the abutting of its vertical surfaces 152,154,156 against corresponding inner vertical surfaces 142,144,146 of clamp body 103, but is free to slide vertically along clamp body inner surfaces 142,144,146. A split angled face 158a, 158b of the threaded wedge 112 opposes a split parallel face 160a, 160b on the floating wedge 114. The faces 158a, 158b split by the threaded bore portion 132 of wedge 112. The floating wedge 114 is restricted vertically by its top surface 162 and bottom surface 164 that slide, respectively, against internal parallel surfaces 166 of the clamp body 103 and surfaces 168a, 168b of track limiters 170a, 170b. Best viewed in FIG. 3B, floating wedge 114 has a width approximately equal to a width of lower jaw 110.

With reference again to FIGS. 1 and 2B, the vertical axle 118 is capable of rotational motion in the direction indicated by arrow 150. As the control knob 116 is turned, the threaded coupling (not shown) between the threads 148 of vertical axle 118 and the threaded bore 132 of the threaded wedge 112 interact to drive the threaded wedge 112 in a downward direction as indicated by arrow 172 and vertical axle 118 upward as indicated by arrow 174. The relative motion induced by rotating control knob 116 first causes lower jaw 110 to retract vertically in the direction of arrow 174 as a result of the mechanical coupling between lower jaw 110 and the pin end 136 (not shown) of the vertical axle 118. Lower jaw 110 is forced to engage the bottom 176 of bedrail 122. FIG. 2C shows bedrail 122 locked in a vertically affixed position between lower jaw 110 and fixed upper jaw(s) 106.

With continued rotation of the control knob 116, surfaces 158a, 158b of threaded wedge 112 will engage surfaces 160a, 160b of floating wedge 114 such that the threaded wedge 112 pushes the floating wedge 114 in the direction of arrow 180 up against the side 178 of the bedrail 122. As threaded wedge 112 is pulled or pushed vertically, surface 177 (shown in FIG. 3) of the floating wedge 114 will be engaged towards or away from the bedrail 122. FIG. 2C shows bedrail 122 locked in a horizontally affixed position between surface 177 (not shown) of the floating wedge 114 and flange(s) 108 of fixed jaw(s) 106 and flange 109 of the lower jaw 110. When the control knob 116 is fully tightened, the parallel surfaces 158a, 158b and 160a, 160b of the horizontal wedges will form a friction lock securing the vertical rotational support 104 both horizontally and vertically. Lower jaw 110 may partially surrounds bedrail 122 and securely engage or bite into the bedrail 122 upon tightening of control knob 116. In alternate embodiments, lower jaw 110 and upper jaw(s) 106 may have jagged, sinusoidal curve, rectangular wave, or toothed profiles.

Figure 4A:
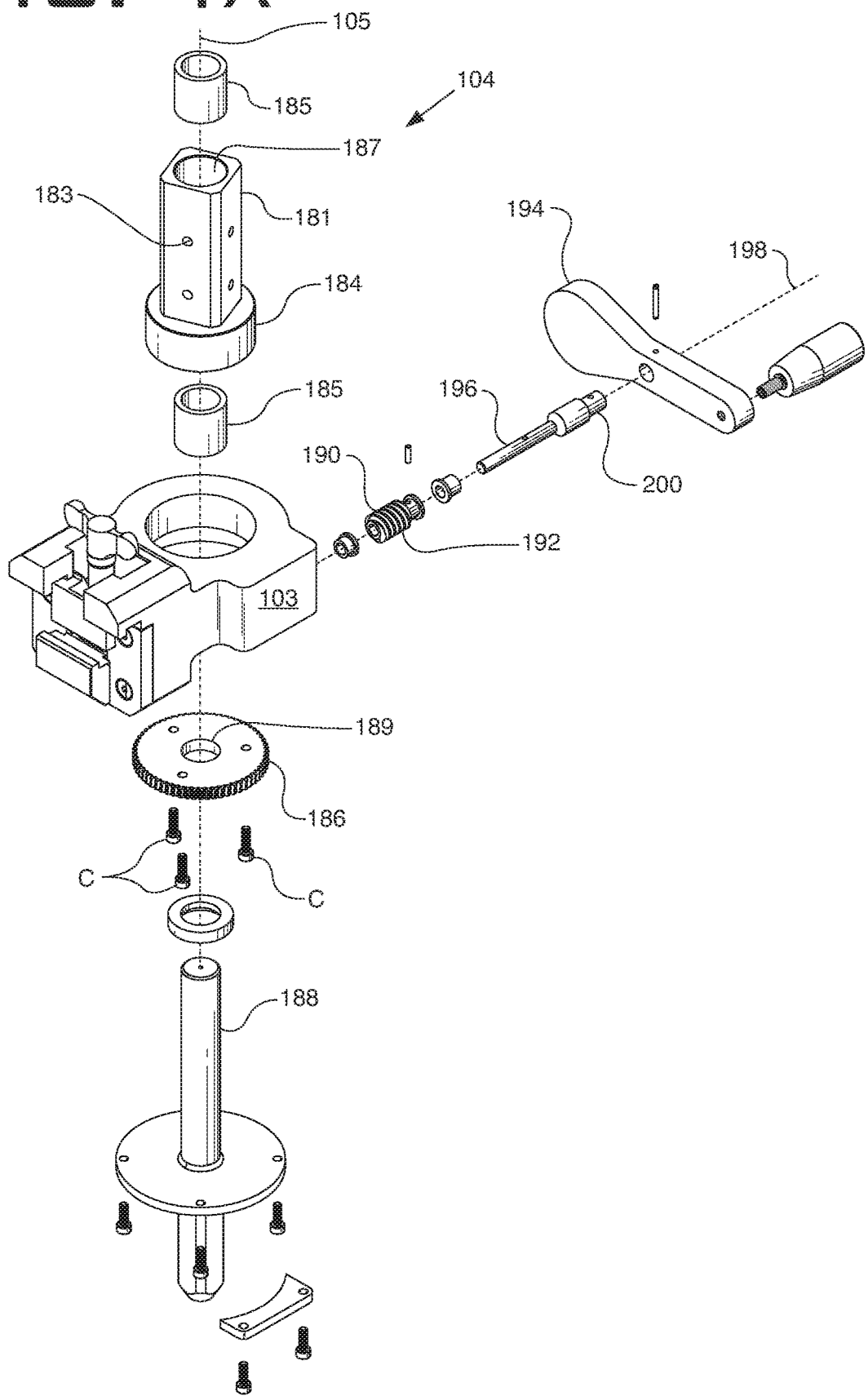
FIGS. 4A and 4B are illustrations of exploded and a cross section view of a vertical support mechanism in accordance with an embodiment of the disclosure.
Figure 4B:
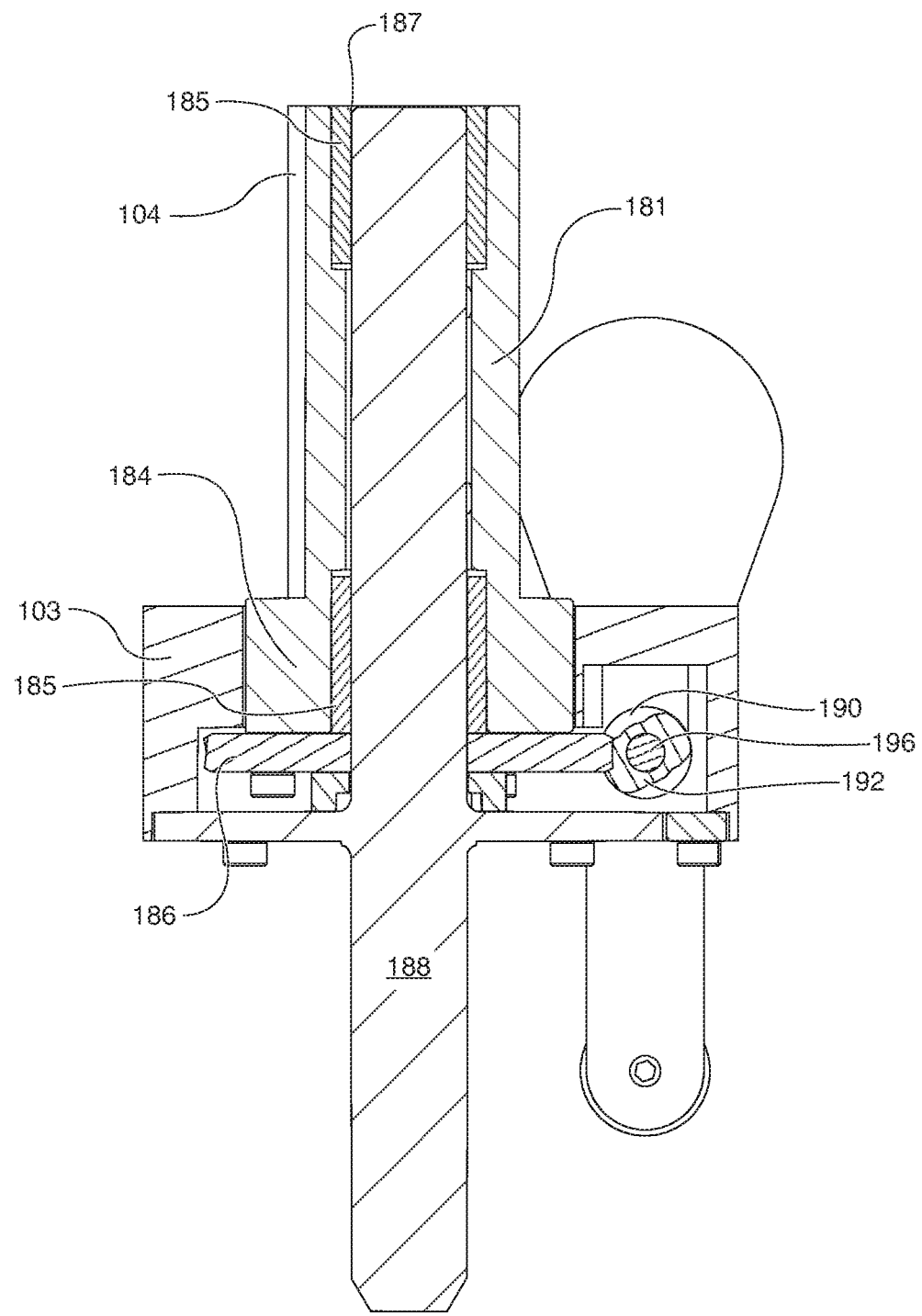

FIG. 4A shows a partially exploded view of an embodiment of a quick release clamp assembly 100, showing the rotational control mechanism 103. FIG. 4B illustrates a cross section view of quick release clamping assembly 100, the clamp body 103 housing a mechanism that translates and controls rotational connector 104, which provides rotational control of a medical device or accessory (not shown) mounted thereto about vertical axis 105. Rotational connector 104 comprises a vertical support 181 that may rests upon the top 182 of the clamp body 103 or nest within the clamp body. The support 181 may include typical features (e.g., apertures 183, pins, clamps, etc.) that facilitate attachment to a medical device or accessory requiring support. Medical instruments may include, among others, instrument trays, surgical devices, IV bags, retractors, arm and leg boards, and the like. The support 181 is secured to a round shaft 184 that may run through the clamp body 103 or nest within the clamp body. The shaft 184 is constrained in all directions except rotationally about the vertical axis 105. Shaft 184 and support 181 may have an elongate opening 187 having recesses for nesting corresponding bearing sleeves 185 disposed therein to smooth rotation. Opening 187 may be sized to receive shaft 188. A gear 186 which is part of a worm drive system is secured to the shaft 184, gear 186 having a central opening 189 sized to receive shaft 188 such that gear 186 may freely rotate around shaft 188. Gear 186 is secured to shaft 184 using mechanical means indicated as "C" in FIG. 4A, such as pins, nails, screws or adhesive for example. In this embodiment, the gear 186 may be a section of a worm gear mechanism, and may be operable coupled to a worm screw such as a double toothed worm screw 190 with a low lead angle 192 and a relatively large gear ratio (approximately 30:1). The double toothed worm screw 190 may be preferable as it reduces back drive while still providing reasonable ratios of rotation of shaft 184, for a given rotation of the worm screw 190. Alternative embodiments may include a single or multiple toothed worm screw 190, with alternate lead angles and gear ratios. The worm drive is generally configured to reduce back drive. This allows for a single handed rotation and self-locking positioning of shaft 184. Stated otherwise, the shaft 184 can be driven by a user interface, such as a crank handle 194, but the user interface cannot be driven by the shaft 184, so the desired position of the shaft 184 does not move upon release of crank handle. An axle 196 runs through the center of the worm screw 190 to a point external to the clamp body 103. The axle 196 is constrained in all directions except rotationally about a horizontal axis 198. Crank handle 194 is secured to an end 200 of the worm screw axle 196, which allows a user to make rotational adjustments to the vertical support 181 in both the clockwise and counter clockwise directions. Anti-back drive properties of the translation and control mechanism remove the need for a second user interface, such as a lock, pin or clamp, which are typically required for similar rotational control mechanisms.

It will be readily appreciated that numerous alternative embodiments of the clamping assembly 100 are possible. For example, as noted above, in addition to varying dimensions of the components, clamping surfaces may have flat or non-flat contours. The gear 186 coupled to the vertical support 181 and the worm screw 190 may be configured at positions distinct from those shown in the figures. In yet other embodiments, the user actuators (control knob 116, crank handle 194) may be implemented as levers, cranks and/or cams. In other embodiments, redundant constraints may be utilized as safety locks for the rail interface mechanism 102 and rotational connector 104.

Whereas many alterations and modifications of the disclosure will no doubt become apparent to a person of ordinary skill in the art after having read the foregoing description, it is to be understood that the particular embodiments shown and described by way of illustration are in no way intended to be considered limiting. No element, act, or instruction used herein should be construed as critical or essential unless explicitly described as such.

What is claimed is:

1. A clamping assembly for adjustably connecting a device to a rail, comprising:
    a clamp body; and
    a rail interface mechanism dimensioned to receive a rail, comprising;
        at least one fixed jaw configured to engage a portion of the rail;
        a second jaw opposing the fixed jaw, constrained to slidable motion along a first direction;
        a rail clamp control having a threaded axle and rotatably coupled to the second jaw;

a floating wedge operatively coupled to the threaded axle and constrained to motion in a direction orthogonal to the first direction;

wherein rotating the rail clamp control causes both the second jaw and the floating wedge to move to engage the rail between the floating wedge, the fixed jaw and the second jaw.

2. The clamping assembly of claim 1 wherein the rail interface mechanism also comprises a threaded wedge, threadably coupled to the threaded axle and operatively coupled to the floating wedge.

3. The clamping assembly of claim 2 wherein the threaded wedge includes an angled wedge face and wherein the floating wedge includes a wedge face parallel to and operatively coupled to the angled wedge face, and wherein rotating the rail clamp control causes the threaded wedge to slide and impart a force from the angled wedge face of the threaded wedge to the wedge face of the floating wedge and urge the floating wedge to move and engage the rail.

4. The clamping assembly of claim 1 wherein the at least one fixed jaw and the second jaw are configured to engage a top and bottom surface of the rail respectively, and the floating wedge is configured to engage a vertical surface of the rail.

5. The clamping assembly of claim 1, wherein the second jaw includes sidewalls that interface with the clamp body to restrict the second jaw from horizontal motion.

6. The clamping assembly of claim 1, wherein the clamp body is coupled to a vertical support mechanism.

7. The clamping assembly of claim 6 wherein the vertical support mechanism includes a vertical support constrained to rotational motion around a longitudinal axis of the vertical support.

8. The clamping assembly of claim 6 wherein the vertical support mechanism comprises:
a vertical support member extending from the clamp body and constrained to rotational motion about a vertical axis by a cylindrical shaft secured on a first end to the support member, the cylindrical shaft extending at least partially through the clamp body;
a shaft gear secured to a second end of the cylindrical shaft;
a horizontally disposed worm screw operably engaging the shaft gear, and including an axle constrained to rotational motion and extending on one end to an area external to the clamp body;
a user control fixated to the end of the worm screw axle, such that rotation of the worm screw axle via the user control permits rotational adjustments to the vertical support member.

9. A clamping assembly for adjustably connecting a device to a rail, comprising:
a clamp body; and
a rail interface mechanism configured to receive and engage a rail, comprising;
a first and second jaw, the second jaw slideable relative to the first jaw;
a rail clamp control having a threaded axle and rotatably coupled to the second jaw; and
a floating wedge operatively coupled to the threaded axle, the floating wedge defining a planar surface configured to engage the rail, the planar surface constrained to motion in a direction orthogonal to the planar surface and between the first and second jaw;
wherein rotating the rail clamp control causes the rail interface mechanism to move the second jaw and the floating wedge to secure the rail therebetween.

10. The clamping assembly of claim 9 wherein the rail interface mechanism also includes a threaded wedge, threadably coupled to the threaded axle, the threaded wedge including an angled wedge face and wherein the floating wedge includes a wedge face parallel to and operatively coupled to the angled wedge face of the threaded wedge, and wherein rotating the rail clamp control causes the threaded wedge to slide and impart a force from the wedge face of the threaded wedge to the wedge face of the floating wedge and urge the floating wedge to move and engage the rail.

11. The clamping assembly of claim 9 wherein the first jaw defines a fixed jaw.

12. The clamping assembly of claim 9 wherein the second jaw is restricted to vertical sliding motion.

13. The clamping assembly of claim 9 wherein the first and second jaw further comprise flanges configured to interface with the rail.

14. The clamping assembly of claim 9 further comprising a vertical support mechanism including a vertical support member constrained to rotational motion around a longitudinal axis of the vertical support.

15. The clamping assembly of claim 14, wherein the vertical support mechanism also comprises:
a shaft gear secured to a second end of the cylindrical shaft;
a horizontally disposed worm screw operably engaging the shaft gear, and including an axle constrained to rotational motion and extending on one end to an area external to the clamp body;
a user control fixated to the end of the worm screw axle, such that rotation of the worm screw axle via the user control permits rotational adjustments to the vertical support member.

16. The clamping assembly of claim 15, wherein the worm screw operably engages the second end of the shaft at a lower lead angle of the worm screw.

17. A clamping assembly for adjustably connecting a device to a rail, comprising:
a clamp body; and
a rail interface mechanism configured to move from a first configuration that receives the rail therein to a second configuration that clamps on the rail, the rail interface mechanism comprising;
a fixed jaw configured to engage a portion of the rail;
a moving jaw opposing the fixed jaw, constrained to translation along a first plane between the first and second configuration;
a wedge construct having a planar surface constrained to translation between the fixed jaw and moving jaw;
a rail clamp control comprised of a threaded axle and rotatably coupled to the moving jaw and operatively coupled to the wedge construct, the rail clamp control configured to move both the moving jaw and the wedge construct between the first and second configuration.

18. The clamping assembly of claim 17 wherein the wedge construct includes a threaded wedge and a floating wedge, the threaded wedge directly coupled to the threaded axle and restricted to translation along the first plane, the floating wedge including the planar surface.

19. The clamping assembly of claim 18 wherein the threaded wedge includes an angled wedge face and wherein the floating wedge includes a wedge face parallel to and operatively coupled to the angled wedge face of the threaded wedge, and wherein rotating the rail clamp control causes the threaded wedge to slide and impart a force from the wedge face of the threaded wedge to the wedge face of the floating wedge and urge the floating wedge towards the second configuration.

20. The clamping assembly of claim 17 wherein the fixed jaw and the moving jaw are configured to engage a top and bottom surface of the rail respectively, and the wedge construct is to engage a vertical surface of the rail.

* * * * *